(12) United States Patent
Hirose

(10) Patent No.: US 8,500,280 B2
(45) Date of Patent: Aug. 6, 2013

(54) OPTICAL IMAGING APPARATUS AND METHOD FOR IMAGING AN OPTICAL IMAGE

(75) Inventor: Futoshi Hirose, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 33 days.

(21) Appl. No.: 13/264,227

(22) PCT Filed: Apr. 20, 2010

(86) PCT No.: PCT/JP2010/057318
§ 371 (c)(1),
(2), (4) Date: Oct. 13, 2011

(87) PCT Pub. No.: WO2010/128630
PCT Pub. Date: Nov. 11, 2010

(65) Prior Publication Data
US 2012/0044455 A1    Feb. 23, 2012

(30) Foreign Application Priority Data

May 8, 2009   (JP) ................................ 2009-113818
Mar. 3, 2010  (JP) ................................ 2010-047052

(51) Int. Cl.
*A61B 3/14*    (2006.01)
*A61B 3/10*    (2006.01)
*A61B 3/00*    (2006.01)

(52) U.S. Cl.
USPC ............ 351/206; 351/205; 351/221; 351/246

(58) Field of Classification Search
USPC ................................................. 351/200–246
See application file for complete search history.

(56) References Cited

U.S. PATENT DOCUMENTS

| | | | |
|---|---|---|---|
| 7,367,672 B2 | 5/2008 | Akita | |
| 7,445,335 B2 | 11/2008 | Su et al. | |
| 7,520,613 B2 | 4/2009 | Saito et al. | |
| 7,540,614 B2 | 6/2009 | Kawashima et al. | |
| 7,758,189 B2 | 7/2010 | Hammer et al. | |

(Continued)

FOREIGN PATENT DOCUMENTS

| | | | |
|---|---|---|---|
| JP | 2007-014569 A | 1/2007 | |
| JP | 2008-220770 A | 9/2008 | |

OTHER PUBLICATIONS

International Preliminary Report on Patentability dated Nov. 9, 2011, in International Application No. PCT/JP2010/057318.

(Continued)

*Primary Examiner* — Mohammed Hasan

(74) *Attorney, Agent, or Firm* — Fitzpatrick, Cella, Harper & Scinto

(57) ABSTRACT

To provide an optical imaging apparatus capable of providing a high lateral resolution in a wide region and easily adjusting prior to imaging for imaging an optical image of an eye to be inspected which is an object, and a method for imaging an optical image. The optical imaging apparatus in which a beam from a light source is used as a measuring beam, and an image of an object is imaged based on intensity of a return beam formed of the measuring beam irradiated to the object has the following: first, an optical device for focusing the measuring beam on the object; next, a aberration detecting device for measuring a aberration of the return beam; and a focus adjusting device for adjusting the optical device based on the aberration detected by the aberration detecting device.

20 Claims, 8 Drawing Sheets

U.S. PATENT DOCUMENTS

| | | |
|---|---|---|
| 7,815,310 B2 | 10/2010 | Su et al. |
| 7,896,496 B2 | 3/2011 | Hammer et al. |
| 2007/0010313 A1 | 1/2007 | Akita |
| 2007/0171366 A1* | 7/2007 | Su et al. ............... 351/205 |
| 2007/0252951 A1 | 11/2007 | Hammer et al. |
| 2008/0158508 A1* | 7/2008 | Kawashima et al. ......... 351/206 |
| 2008/0225228 A1* | 9/2008 | Saito et al. ............... 351/206 |
| 2008/0278683 A1 | 11/2008 | Su et al. |
| 2009/0091766 A1 | 4/2009 | Hirose |
| 2009/0285354 A1 | 11/2009 | Hirose et al. |
| 2010/0103374 A1 | 4/2010 | Hirose et al. |
| 2010/0231858 A1 | 9/2010 | Su et al. |
| 2010/0253908 A1 | 10/2010 | Hammer et al. |
| 2010/0321700 A1 | 12/2010 | Hirose et al. |
| 2011/0152845 A1 | 6/2011 | Hammer et al. |
| 2011/0164220 A1 | 7/2011 | Su et al. |
| 2011/0234975 A1 | 9/2011 | Hirose |
| 2011/0273668 A1 | 11/2011 | Hirose |
| 2011/0301455 A1 | 12/2011 | Numajiri et al. |

OTHER PUBLICATIONS

"Ultrahigh-resolution optical coherence tomography with monochromatic and chromatic aberration correction", Opt Express 16, 8126 (2008).

Notification of Transmittal of the International Search Report and the Written Opinion of the International Searching Authority, or the Declaration dated Aug. 13, 2010, forwarding the International Search Report and the Written Opinion of the International Searching Authority ("ISR") in counterpart International Application No. PCT/JP2010/057318.

* cited by examiner

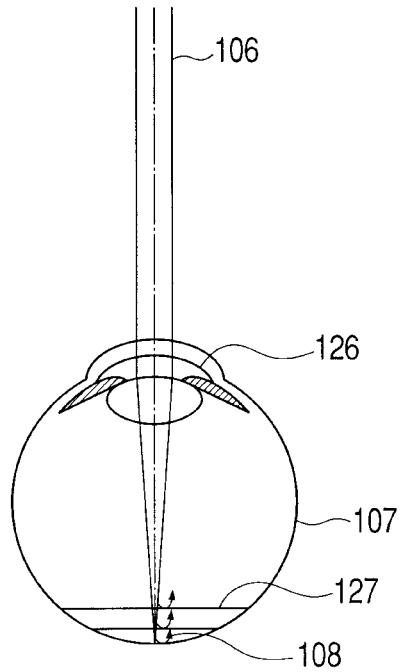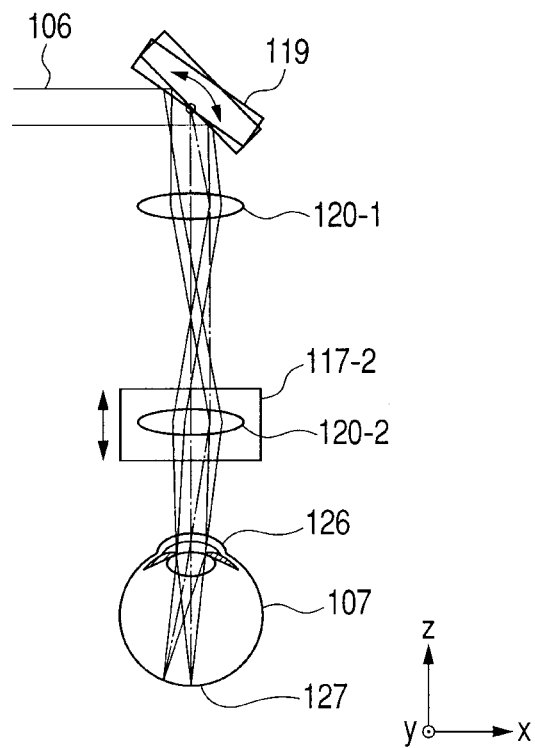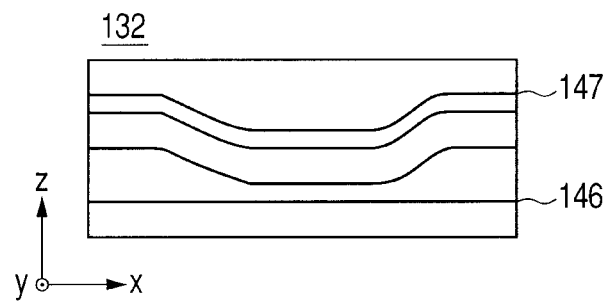

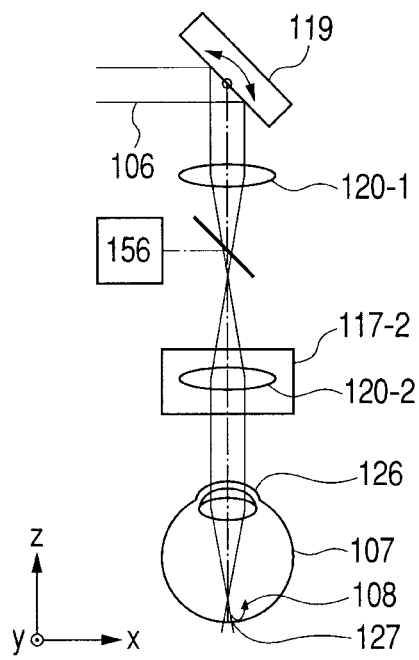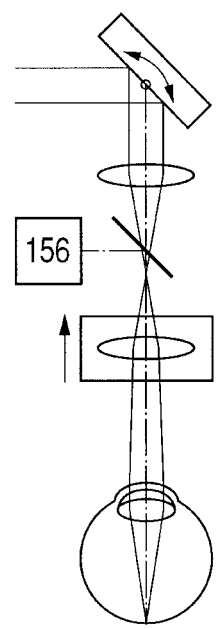
FIG. 3A  FIG. 3B
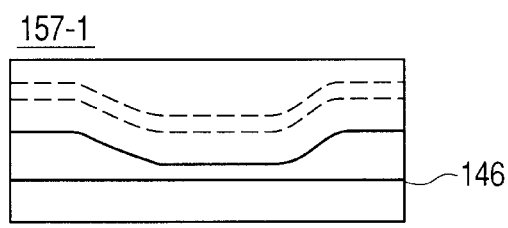
FIG. 3C
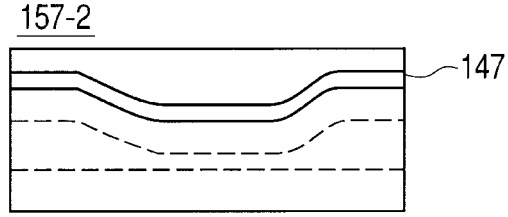
FIG. 3D
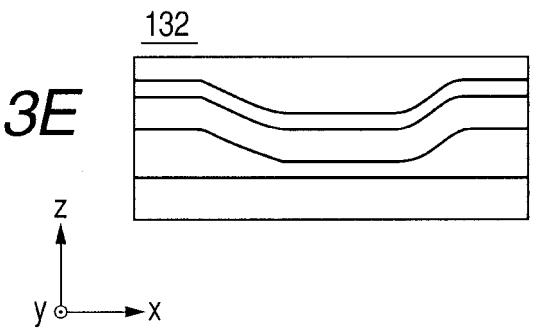
FIG. 3E

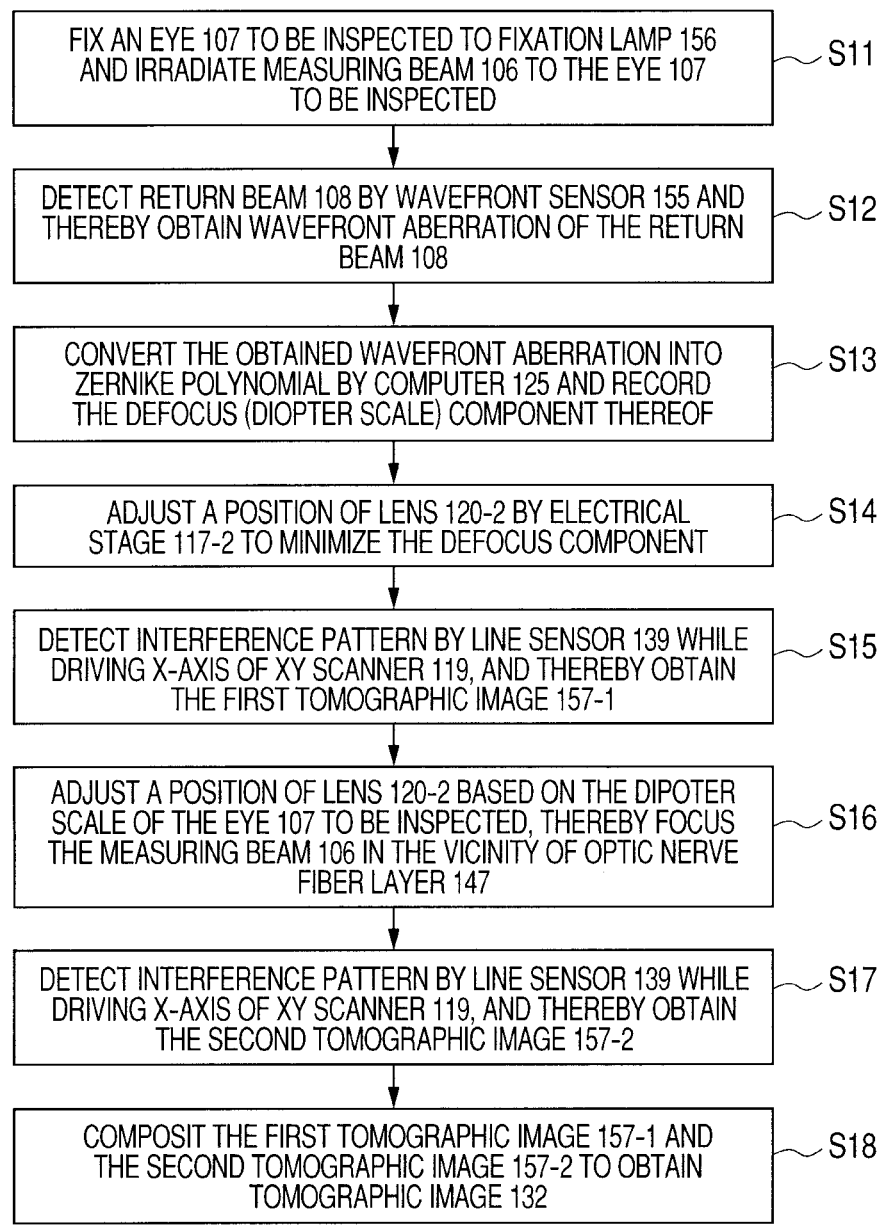

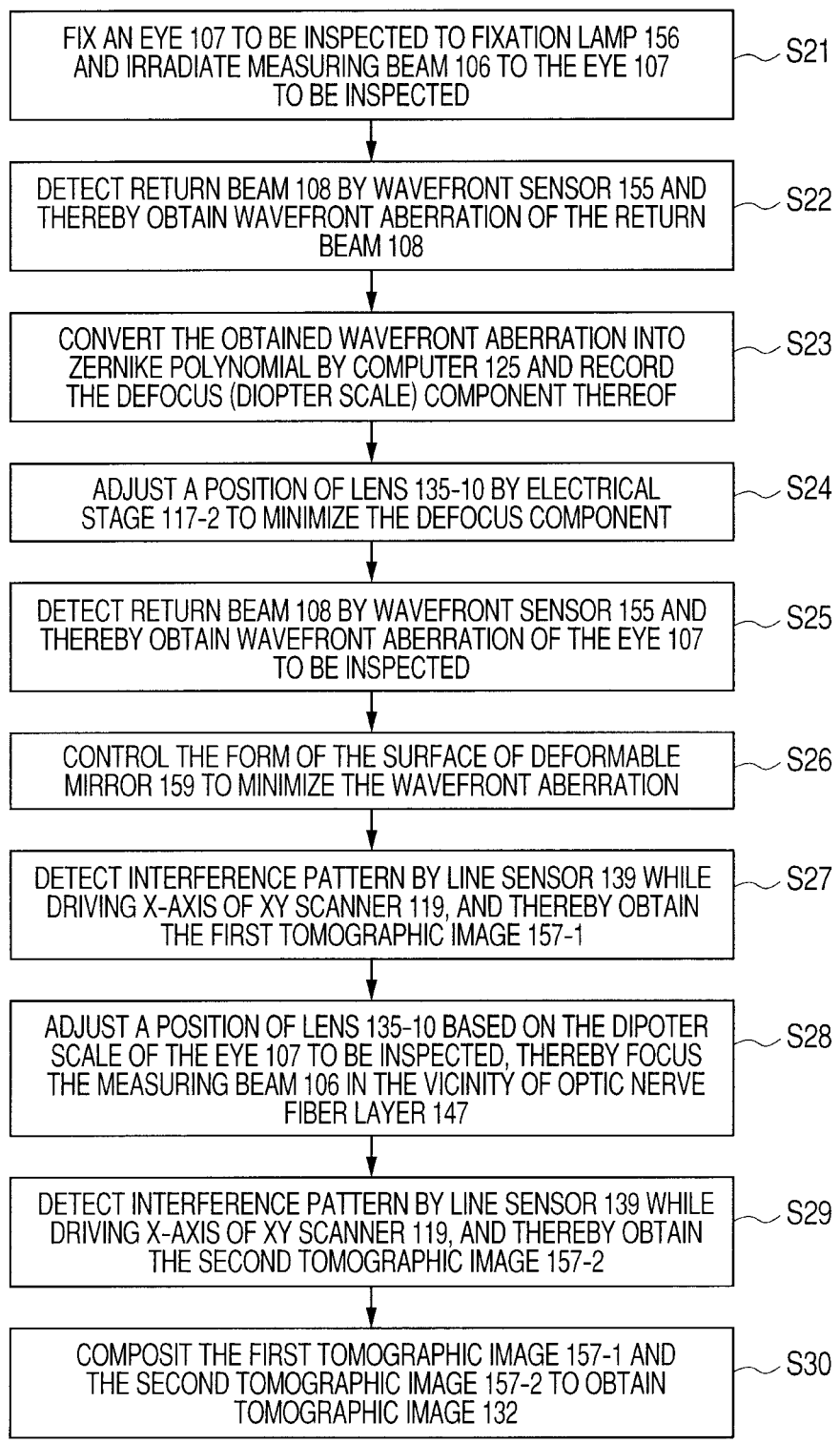

OPTICAL IMAGING APPARATUS AND METHOD FOR IMAGING AN OPTICAL IMAGE

TECHNICAL FIELD

The present invention relates to an optical imaging apparatus and a method for imaging an optical image, and particularly to an optical imaging apparatus and a method for imaging an optical image used for ophthalmologic diagnosis and treatment.

BACKGROUND ART

Optical Coherent Tomography (OCT) using an interference phenomenon of multi-wavelength light is a method for acquiring a tomographic image of a sample (particularly the fundus) with a high resolution. An apparatus for imaging a tomographic image by using such OCT is hereinafter called "an OCT apparatus". Recently, by enlarging the beam diameter of a measuring beam in an OCT apparatus of the Fourier Domain system, a tomographic image of the retina can be provided with an improved lateral the resolution. However, as the beam diameter of the measuring beam has been enlarged, there is, at acquisition of a tomographic image of the retina, presented a problem of decrease in the S/N ratio and resolution of the tomographic image due to an aberration in an eye to be inspected. To resolve the problem, an adaptive optics OCT apparatus having adaptive optics has been developed in which an aberration in an eye to be inspected is measured by a wavefront sensor in real time, the aberration, generated in the eye to be inspected, of a measuring beam or a return beam are corrected by a wavefront correcting device, and thereby the apparatus enables a tomographic image being provided with a high lateral resolution.

Regarding an apparatus using such adaptive optics, Japanese Patent Application Laid-Open No. 2007-14569 proposes an ophthalmologic imaging apparatus capable of acquiring an image of the fundus by using adaptive optics, a polygon mirror, a galvano-mirror, etc. in a scanning laser ophthalmoscope (SLO apparatus). This ophthalmologic imaging apparatus is adapted so that an aberration in an eye to be inspected is detected and an aberration of a return beam formed of a measuring beam irradiated to a retina is corrected by using the adaptive optics, and allows a lateral resolution to be prevented from being degraded. Also, "Ultrahigh-resolution optical coherence tomography with monochromatic and chromatic aberration correction", Opt. Express 16, 8126 (2008) describes an OCT apparatus of the Fourier Domain system in which both of a high lateral resolution and a high longitudinal resolution are intended to be coexistent by using the adaptive optics and a chromatic aberration correction lens. Here, it is tried to reduce speckles and improve the contrast of a tomographic image by measuring and correcting an aberration of a measuring beam and a return beam generated in an eye to be inspected using the adaptive optics, and further averaging obtained tomographic images of the retina.

DISCLOSURE OF THE INVENTION

An ophthalmic apparatus having the conventional adaptive optics described above is, as described above, adapted so that it can provide an image with a high lateral resolution by measuring and correcting an aberration of a measuring beam and a return beam generated in an eye to be inspected using the adaptive optics. However, enlarging the beam diameter of a measuring beam decreases the depth of focus, but an adverse effect caused due to the enlarging cannot be excluded in these conventional examples, and the enlargement of the beam diameter cannot necessarily provide a satisfactory advantage for acquiring an image with a high resolution. Further, prior to imaging, optical adjustment is necessary to be suitable for each of eyes to be inspected as objects, which forms restriction to imaging.

An object of the present invention is, in view of the problems described above, to provide an optical imaging apparatus capable of providing a high lateral resolution in a wide region and easily adjusting prior to imaging for imaging an eye to be inspected as an object, and a method for imaging an optical image. The present invention provides an optical imaging apparatus adapted as follows and a method for imaging an optical image. The optical imaging apparatus of the present invention is an optical imaging apparatus in which a beam from a light source is used as a measuring beam and an image of an object is imaged using a return beam formed of the measuring beam irradiated to the object, characterized by comprising: an optical device for focusing the measuring beam on the object, an aberration detecting device for measuring an aberration of the return beam, and a focus adjusting device for adjusting the optical device based on the aberration detected by the aberration detecting device. Further, the method for imaging an optical image according to the present invention is a method for imaging an optical image in which a beam from a light source is used as a measuring beam, and an image of an object is imaged using a return beam formed of the measuring beam irradiated to the object, characterized by comprising: a first step of measuring an aberration of the object using an aberration detecting device, a second step of converting the aberration into a polynomial having a term including a defocus component, and recording the defocus component of the aberration expressed in the polynomial, and a third step of adjusting a focus adjusting device focusing the measuring beam on the object based on the defocus component. The present invention can realize an optical imaging apparatus capable of providing a high lateral resolution in a wide region and easily adjusting prior to imaging for imaging an eye to be inspected as an object, and a method for imaging an optical image.

Further features of the present invention will become apparent from the following description of exemplary embodiments with reference to the attached drawings.

BRIEF DESCRIPTION OF THE DRAWINGS

FIGS. 2A, 2B and 2C illustrate a method for acquiring an image of the OCT apparatus in the first exemplary embodiment of the present invention.

FIGS. 3A, 3B, 3C, 3D and 3E illustrate a method for acquiring a tomographic image of the OCT apparatus in the first exemplary embodiment of the present invention.

FIG. 4 is a flow chart for illustrating a procedure for acquiring a tomographic image of the OCT apparatus in the first exemplary embodiment of the present invention.

FIG. 7 is a flow chart for illustrating a procedure for acquiring a tomographic image of the OCT apparatus in the second exemplary embodiment of the present invention.

BEST MODES FOR CARRYING OUT THE INVENTION

Embodiments of the present invention will be described with reference to exemplary embodiments below.

Embodiments

Exemplary Embodiment 1

A first exemplary embodiment describes an OCT apparatus to which the present invention is applied. Particularly, here, there is given a description of an OCT apparatus with a high lateral resolution and capable of imaging both of a planar image (SLO image) and a tomographic image (OCT image) of an eye to be inspected. In this exemplary embodiment, an optical imaging apparatus is adapted so that a measuring beam from a light source is irradiated to an object, and a planar image and a tomographic image of the object are imaged based on light intensity of a return beam formed of the measuring beam irradiated to the object. Particularly, the beam from the light source is split into a measuring beam and a reference beam, and a return beam formed of the measuring beam irradiated to the object and the reference beam traveling through a reference light path are combined to interfere with each other, and then a tomographic image of the object is provided based on intensity of an interference signal formed from the interference. At this time, an OCT apparatus of the Fourier Domain system is adapted so that a plurality of tomographic images having a different focus position are composited to form a single tomographic image, and thereby a good tomographic image can be provided regardless of a diopter scale of an eye to be inspected.

Figure 1:
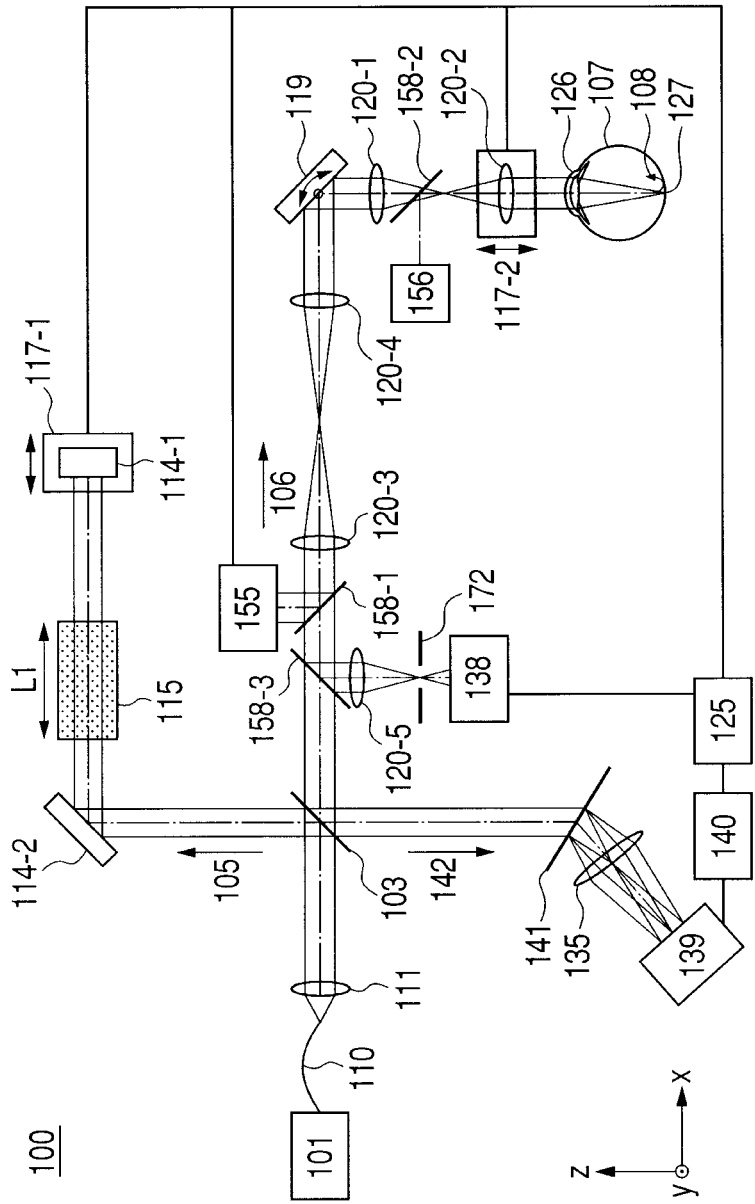
FIG. 1 illustrates a whole configuration of an OCT apparatus in a first exemplary embodiment of the present invention.

Referring to FIG. 1, first, a whole, schematic configuration of an optical system of an OCT apparatus in the present exemplary embodiment is specifically described. An OCT apparatus 100 of the exemplary embodiment is, as illustrated in FIG. 1, a Michelson interference system as a whole. In FIG. 1, a beam emitted from a light source 101 is split into a reference beam 105 and a measuring beam 106 by a beam splitter 103. The measuring beam 106 is reflected or scattered by an eye 107 to be inspected as an object to be observed, forming a return beam 108, which comes back and is combined with the reference beam 105 by the beam splitter 103. The reference beam 105 and the return beam 108, after being combined, are dispersed into their wavelength components by a transmission grating 141 and projected on a line camera 139. The line camera 139 converts light intensities into a voltage for each of positions (wavelengths), and these signals are used to form a tomographic image of the eye 107 to be inspected. Also, a part of the return beam 108 is projected to a detector 138 by a beam splitter 158-3. The detector 138 converts light intensities into voltages, and these signals are used to form a planar image of the eye 107 to be inspected. In the exemplary embodiment, the whole optical system is adapted mainly using a refractive optical system using lenses, but may be also adapted using a reflective optical system using spherical mirrors instead of the lenses. Further, a part of the optical system may be adapted using an optical fiber.

Next, details of the light source 101 are described. The light source 101 is a Super Luminescent Diode (SLD), which is a representative low-coherence light source. The wavelength is 830 nm, and the bandwidth is 50 nm. Here, the bandwidth is an important parameter because it has an effect on a resolution of the obtained tomographic image in a direction of the optical axis. Also, the type of light source selected here is a SLD, but it may be any type which can emit low-coherence light, and Amplified Spontaneous Emission (ASE), etc. may be used. Further, near-infrared light is, with consideration for a measurement of the eye, suitable for the wavelength. Further, the wavelength is desirably as short as possible because it has an effect on a resolution of the obtained tomographic image in a lateral direction, and here 830 nm has been selected as the wavelength. Another wavelength may be selected dependent on a position to be measured of an object. The beam emitted from the light source 101 passes through a single-mode fiber 110, and is directed to a lens 111 and adjusted to be a collimated beam having the beam diameter of 2 mm.

Next, a light path of the reference beam 105 is described. The reference beam 105 split by the beam splitter 103 is projected on a mirror 114-2 to turn its direction, projected on a mirror 114-1, and reflected therefrom, and then goes back toward the beam splitter 103. Next, the reference beam 105 passes through the beam splitter 103 and is directed to the line camera 139. Here, a dispersion compensation glass compensates the reference beam 105 for dispersion produced when the measuring beam 106 goes to and comes back from the eye 107 to be inspected. It is, here, supposed that a representative value of the average diameter of Japanese eyeballs, L1=23 mm, is set. Further, an electrical stage 117-1 can move in the directions shown by the arrow, and adjust and control the light path length of the reference beam 105. Also, the electrical stage 117-1 can be controlled by a personal computer 125 at a high speed.

Next, a light path of the measuring beam 106 is described. The measuring beam 106 split by the beam splitter 103 passes through beam splitters 158-3 and 158-1, and lenses 120-3 and 120-4 and is projected on a mirror of an XY scanner 119. Here, for the simplicity, the XY scanner 119 is illustrated as one mirror, but actually the XY scanner 119 has two mirrors, a mirror for X scanning and a mirror for Y scanning, disposed close to each other therein, and scans the retina 127 in the direction perpendicular to the optical axis in the raster scan mode. Also, the center of the measuring beam 106 is adjusted to coincide with the rotation center of the mirror of the XY scanner 119. Lenses 120-1 and 120-2 form an optical system for scanning the retina 127 and play a role in scanning the retina 127 with the measuring beam 106 using the vicinity of the cornea 126 as a pupil of the optical system. Here, the focus distances of the lenses 120-1 and 120-2 are 50 mm and 40 mm, respectively. Here, the measuring beam 106 has the beam diameter of 2 mm, and the depth of focus of about 250 μm in the eye 107 to be inspected. The beam diameter may be more enlarged to acquire a tomographic image with a higher resolution. However, because the depth of focus is inversely proportional to the square of the beam diameter, optical adjustment becomes difficult. Further, an electrical stage 117-2 can move in the directions shown by the arrow, and adjust and control a position of the lens 120-2 which is a focus lens attached thereto. By adjusting the position of the lens 120-2, the measuring beam 106 can be focused on a predetermined layer in the retina 127 of the eye 107 to be inspected, and observing can be performed. Further, the case of the eye 107 to be inspected having a refractive error can be addressed. When the measuring beam 106 is projected in the eye 107 to be inspected, it is reflected or scattered by the retina 127 to form the return beam 108, which is reflected by the beam splitter 103 and directed to the line camera 139. Also, a part of the return beam 108 is reflected by the beam splitter 158-3 and directed to the detector 138 through a lens 120-5. Here, a shield plate 172 has a pin hole and plays a role in blocking an unnecessary beam, i.e. the beam not focused on the retina 127, in the return beam 108. Also, the pin hole of the shield plate 172 is disposed to become conjugate with a focus position of the lens 120-5. Also, the diameter of the pin hole is, for example, 50 μm. The detector 138 used is, for example, an Avalanche Photo Diode (APD) which is a high-speed, high-sensitivity optical sensor. Here, the electrical stage 117-2 can be controlled by the personal computer 125, which characterizes the present embodiment.

Also, a part of the return beam 108 split by the beam splitter 158-1 is projected on a wavefront sensor 155 (as an aberration detecting device of the present embodiment), and an aberration of the return beam 108 is measured. The wavefront sensor 155 is electrically connected to the personal computer 125. The lenses 120-1, 120-2, 120-3 and 120-4 are disposed so that the cornea 126, the XY scanner 119 and the wavefront sensor 155 become approximately optically conjugate with each other, and an aberration in the eye 107 to be inspected can be measured by the wavefront sensor 155. Further, the position of the lens 120-2 is adjusted and controlled based on the obtained aberration so that the measuring beam 106 can be focused on a predetermined layer in the retina 127. Here, the lens 120-2 used is a spherical lens, but a cylindrical lens may be used for the lens 120-2 dependent on an aberration (refractive error) in the eye 107 to be inspected. Also, another lens may be added to the light path of the measuring beam 106. A cylindrical lens can effectively correct the astigmatism in a Zernike polynomial, and also is effective in the case where the eye 107 to be inspected is astigmatic.

Next, a configuration of a measuring system in the OCT apparatus of the exemplary embodiment is described. The OCT apparatus 100 can provide a tomographic image (OCT image) formed of intensities of an interference signal generated by a Mickelson interference system. This measuring system is described. A part of the return beam 108 formed of a beam reflected or scattered by the retina 127 is reflected by the beam splitter 103. Here, the reference beam 105 and the return beam 108 are adjusted to be combined with each other at the back of the beam splitter 103. Then, the combined beam 142 is dispersed into its wavelength components by the transmission grating 141, which are condensed by a lens 135, and light intensities are converted into a voltage for each of positions (wavelengths) by the line camera 139. Specifically, an interference pattern in a spectral region in the wavelength axis will be observed on the line camera 139.

The obtained group of voltage signals are converted into digital values by a frame grabber 140, which are data processed by the personal computer 125 to form a tomographic image. In the exemplary embodiment, the line camera 139 has 1024 pixels and can provide intensities of the combined beam 142 for each of wavelengths (1024 division). Also, the OCT apparatus 100 can provide a planar image (SLO image) formed of intensities of the return beam 108. Then, a measuring system for the purpose is described. A part of the return beam 108 which is a beam reflected or scattered by the retina 127 is reflected by the beam splitter 158-3. The reflected beam, after an unnecessary beam therein is blocked by the shield plate 172, arrives at the detector 138, and light intensities are converted into electrical signals. The obtained electrical signals are data processed in synchronization with a scan signal by the personal computer 125 to form a planar image. Also, a part of the return beam 108 split by the beam splitter 158-1 is projected on the wavefront sensor 155, and an aberration of the return beam 108 is measured. The wavefront sensor 155 is of the Shack-Hartmann system. The obtained aberration is expressed in a Zernike polynomial, which expresses an aberration of the eye 107 to be inspected. The Zernike polynomial includes terms of tilt, defocus, astigmatism, coma, trefoil, etc.

Next, a method for acquiring a tomographic image using an OCT apparatus is described. The OCT apparatus 100 controls the XY scanner 119 so that the line camera 139 acquires an interference pattern, and thereby a tomographic image of the retina 127 can be provided (see FIG. 1). Here, with reference to FIGS. 2A, 2B and 2C, a method for acquiring a tomographic image of the retina 127 (plane parallel to the optical axis) is described. FIG. 2A is a schematic view of an eye 107 to be inspected, and illustrates a situation in which the eye 107 to be inspected is observed by the OCT apparatus 100. As illustrated in FIG. 2A, when the measuring beam 106 is projected through the cornea 126 on the retina 127, it is reflected or scattered at various positions to form the return beam 108, which arrives at the line camera 139 with a time delay at each of positions. Here, if the light source 101 has a wide bandwidth and a short coherence length, and accordingly the light path length of the reference light path is approximately equal to that of the measuring light path, then the line camera 139 can detect an interference pattern. As described above, what is acquired by the line camera 139 is an interference pattern in a spectral region in the wavelength axis. Next, the interference pattern which is information in the wavelength axis is converted into an interference pattern in the light frequency axis with consideration for characteristics of the line camera 139 and the transmission grating 141. Further, the converted interference pattern in the light frequency axis is inversely Fourier transformed, and thereby information in the depth direction can be provided.

Further, as illustrated in FIG. 2B, by detecting an interference pattern while driving X axes of the XY scanner 119, an interference pattern can be provided for each position of each X axis, that is, information for each position of each X axis in the depth direction can be provided. As the result, a two-dimensional distribution of intensities of the return beam 108 in the XZ plane can be provided, which is namely a tomographic image 132 (see FIG. 2C). Originally, the tomographic image 132 is, as described above, an array in which intensities of the return beam 108 are arranged, and, for example, the intensities are displayed in a gray scale. In FIG. 2C, only the boundaries of the obtained tomographic image are displayed to make an emphasis. The retinal pigment epithelium is shown by the number 146, and the optic nerve fiber layer is shown by the number 147. Next, a method for acquiring a planar image using an OCT apparatus is described. The OCT apparatus 100 controls the XY scanner 119 so that the detector 138 detects intensities of the return beam 108, and thereby a planar image of the retina 127 can be provided (see FIG. 1). Here, with reference to FIGS. 2A and 2B, a method for acquiring a planar image of the retina 127 (plane perpendicular to the optical axis) is described. FIG. 2A is a schematic view of an eye 107 to be inspected, and illustrates a situation in which the eye 107 to be inspected is observed by the OCT apparatus 100. As illustrated in FIG. 2A, when the measuring beam 106 is projected through the cornea 126 on the retina 127, it is reflected or scattered at various positions to form the return beam 108, which arrives at the detector 138. Further, as illustrated in FIG. 2B, by detecting intensities of the return beam 108 while driving X axes of the XY scanner 119, information for each position of each X axis can be provided.

Further, by detecting intensities of the return beam 108 while driving Y axes of the XY scanner 119, a two-dimensional distribution of intensities of the return beam 108 in the XY plane can be provided, which is namely a planar image.

Next, there is given a description of a procedure which characterizes the present embodiment for acquiring a tomographic image using an OCT apparatus with reference to FIGS. 1, 3A, 3B, 3C, 3D, 3E, and 4. Here, a procedure for acquiring a tomographic image is described, but a similar procedure can be also applied to acquiring a planar image. Here, as illustrated in FIG. 1, the OCT apparatus 100 controls the position of the lens 120-2 using the electrical stage 117-2, based on an aberration of the eye 107 to be inspected obtained by the wavefront sensor 155. According to this, a plurality of tomographic images are acquired, and these tomographic images are composited with each other, and thereby a tomographic image can be provided. Here, the case where two tomographic images are acquired is described, but the number of tomographic images to be acquired may be any number. Particularly, if the beam diameter of the measuring beam 106 is large, the depth of focus of the measuring beam 106 becomes short, and accordingly acquiring and compositing many tomographic images are effective.

FIGS. 3A, 3B, 3C, 3D and 3E illustrate procedures of the OCT apparatus 100 for acquiring a tomographic image. Here, as illustrated in FIGS. 3A, 3B, 3C, 3D and 3E, a device for acquiring a tomographic image of the retina 127 in a myopic eye 107 to be inspected is adapted. Of course, if the eye 107 to be inspected is hyperopic or astigmatic, a similar device may be applied. The method for acquiring a tomographic image is such that the following steps (1) to (6) are, for example, successively executed in this order. Alternatively, the steps may return suitably. FIG. 4 is a flow diagram for illustrating a procedure for acquiring a tomographic image described above.

(1) At step 1 (S11 in FIG. 4), while an eye 107 to be inspected is fixed to a fixation lamp 156 (fixation target), the measuring beam 106 is irradiated to the eye 107 to be inspected. Here, the position of the lens 120-2 is adjusted so that the measuring beam 106 is irradiated to the eye 107 to be inspected while being kept in a collimated beam (see FIG. 3A). Then, at step 2 (S12 in FIG. 4), the return beam 108 is measured by the wavefront sensor 155, and thereby an aberration of the return beam 108 is obtained (first step).

(2) At step 3 (S13 in FIG. 4), the obtained aberration is converted into a Zernike polynomial by the personal computer 125, and a defocus component thereof is recorded in memory (second step). This expresses a diopter scale of the eye 107 to be inspected.

(3) At step 4 (S14 in FIG. 4), the position of the lens 120-2 is adjusted using the electrical stage 117-2 so that the defocus component is minimized (third step). Here, the measuring beam 106 is kept focused on the vicinity of the retinal pigment epithelium 127 (not shown) (see FIG. 3B). For example, if the diopter scale of the eye 107 to be inspected is—5D, the position of the lens 120-2 is moved to the side of the lens 120-1 by 8 mm.

(4) At step 5 (S15 in FIG. 4), by detecting an interference pattern by the line sensor 139 while driving X axes of the XY scanner 119, a first tomographic image 157-1 (XZ plane) is obtained (see FIG. 3C). Here, dashed lines in the tomographic image 157 schematically illustrate that a lateral resolution and a contrast are low. That is, it is illustrated that the tomographic image 157-1 is well imaged at the vicinity of the retinal pigment epithelium 146.

(5) At step 6 (S16 in FIG. 4), the electrical stage 117-2 is controlled using the personal computer 125 to adjust the position of the lens 120-2 so that the measuring beam 106 is focused on the vicinity of the optic nerve fiber layer 147 (fifth step). Here, a displacement magnitude of the lens 120-2 is determined based on a diopter scale of the eye 107 to be inspected detected in the step (2). Then, at step 7 (S17 in FIG. 4), similar to the step (4) described above, a second tomographic image 157-2 is obtained (see FIG. 3D).

(6) At step 8 (S18 in FIG. 4), the first tomographic image 157-1 and the second tomographic image 157-2 are composited with each other to obtain a tomographic image 132 (see FIG. 3E). Here, the tomographic image 132 shows a good resolution and a good contrast in the whole measured region.

As described above, by adapting a focus adjusting device for adjusting a focus lens based on an aberration, the focus lens can be adjusted so that an aberration contained in the object itself is measured, and the aberration can be corrected. As the result, a planar image and a tomographic image can be provided with a high lateral resolution and a high measurement sensitivity. Also, a focused state can be quantified, and thereby the focus lens can be easily adjusted, and accordingly an adjustment prior to imaging can be easily performed. Also, the focus lens can be adjusted based on a defocus component. Note that the case based on the defocus component has been described in the procedures described above, but it can be adapted so that the focus lens is adjusted based on at least any one of the defocus component and the astigmatic component. It is particularly effective when a cylindrical lens is used for the focus lens. As a result, the focus lens can be properly adjusted even when the eye to be inspected is myopic, hyperopic or astigmatic. Also, there can be provided the fixation target to which the eye to be inspected as an object is fixed, and thereby a tomographic image can be provided without a blur. Also, there can be provided a construction in which a single tomographic image is obtained by compositing a plural of tomographic images with different focus positions, and thereby the tomographic image can be provided with a high lateral resolution in a wide region in a direction of the optical axis.

Exemplary Embodiment 2

Figure 5:
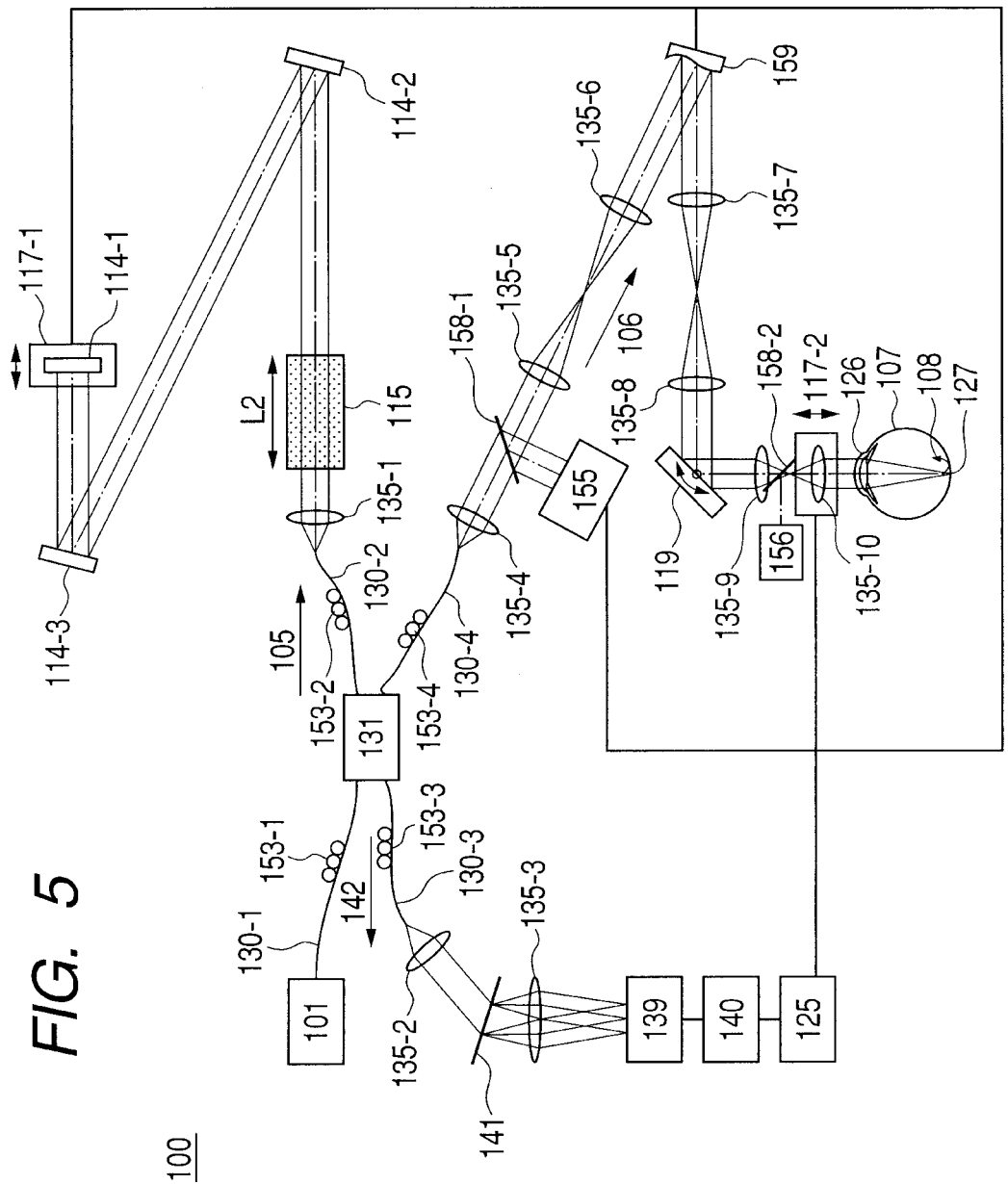
FIG. 5 illustrates a whole configuration of an OCT apparatus in a second exemplary embodiment of the present invention.

A second exemplary embodiment describes an OCT apparatus to which the present invention is applied. Here, particularly, there is given a description of an OCT apparatus with a high lateral resolution for imaging a tomographic image (OCT image) of an eye to be inspected. The present exemplary embodiment provides an OCT apparatus of the Fourier Domain system for acquiring a tomographic image by correcting an aberration, generated in the eye to be inspected, of a measuring beam or a return beam are inspected using a deformable mirror (as an aberration correcting device of the present embodiment), and the OCT apparatus is adapted so that a good tomographic image can be provided regardless of a diopter scale and/or an aberration of the eye to be inspected. Referring to FIG. 5, first, there is given a description of a whole, schematic configuration of an optical system of an OCT apparatus in the exemplary embodiment. In FIG. 5, a similar component to that of the first exemplary embodiment in FIG. 1 is designated by an identical symbol, and a description of a common part is omitted. In FIG. 5, an optical coupler is designated by the number 131, and lenses are designated by the numbers 135-1, 135-2, 135-3, 135-4, 135-5, 135-6, 135-7, 135-8, 135-9 and 135-10. Single-mode fibers are designated by the numbers 130-1, 130-2, 130-3 and 130-4, and polarization controllers are designated by the numbers 153-1, 153-2, 153-3 and 153-4. A deformable mirror is designated by the number 159.

An OCT apparatus 100 of the exemplary embodiment is, as illustrated in FIG. 5, a Michelson interference system as a whole. In FIG. 5, a beam emitted from a light source 101 passes through the optical fiber 130-1 and is split into a reference beam 105 and a measuring beam 106 with the ratio of 90:10 by the optical coupler 131. The measuring beam 106 is directed through the optical fiber 130-4, the deformable mirror 159, an XY scanner 119, etc. to an eye 107 to be inspected as an object to be observed. Further, the measuring beam 106 is reflected or scattered at the eye 107 to be inspected to form a return beam 108, which comes back and is combined with the reference beam 105 by the optical coupler 131. The reference beam 105 and the return beam 108, after being combined, are projected on the line camera 139, and the obtained light intensities are used to form a tomographic image of the eye 107 to be inspected.

Next, details of the light source 101 are described. The light source 101 is a Super Luminescent Diode (SLD) which is a representative, low-coherence light source, and similar to the light source 101 of the first exemplary embodiment, and accordingly a description thereof is omitted. The beam emitted from the light source 101 passes through the single-mode fiber 130-1, and is directed to the optical coupler 131 and split into beams with the ratio of 90:10, which are the reference beam 105 and the measuring beam 106, respectively.

Next, a light path of the reference beam 105 is described. The reference beam 105 split by the optical coupler 131 passes through the single-mode fiber 130-2 and is directed to the lens 135-1 and adjusted to be a collimated beam having the beam diameter of 2 mm. Next, the reference beam 105 is directed through the mirrors 114-2 and 114-3 to the mirror 114-1 which is a reference mirror. Next, the reference beam 105 is reflected by the mirror 114-1 and directed back to the optical coupler 131. Here, a dispersion compensation glass 115 through which the reference beam 105 passed compensates the reference beam 105 for dispersion produced when the measuring beam 106 goes to and comes back from the eye 107 to be inspected through the lenses 135-4, 135-5, 135-6, 135-7, 135-8, 135-9 and 135-10. The dispersion compensation glass 115 has the length of L2, and here, it is set to L2=50 mm. Further, an electrical stage 117-1 can move in the directions shown by the arrow, and adjust and control the light path length of the reference beam 105. Also, the electrical stage 117-1 is controlled by a personal computer 125.

Next, a light path of the measuring beam 106 is described. The measuring beam 106 split by the optical coupler 131 passes through the single-mode fiber 130-4 and is directed to the lens 135-4 and adjusted to be a collimated beam having the beam diameter of 2 mm. The measuring beam 106 passes through the beam splitter 158-2 and the lenses 135-5 and 135-6, and is projected on the deformable mirror 159. Here, the deformable mirror 159 is a mirror device for correcting an aberration of the measuring beam 106 and the return beam 108 by changing the mirror form thereof as desired, based on an aberration detected by the wavefront sensor 155. In this embodiment the deformable mirror has been used as a device for correcting an aberration, but the device may be any device capable of correcting an aberration, and a spatial light modulator using liquid crystal, etc. may be used. Next, the measuring beam 106 passes through the lenses 135-7 and 135-8, and is projected on a mirror of the XY scanner 119. In this embodiment, the XY scanner 119 is, for the simplicity, illustrated as one mirror, but actually the XY scanner 119 has two mirrors, a mirror for X scanning and a mirror for Y scanning, disposed close to each other therein, and scans the retina 127 in the direction perpendicular to the optical axis in the raster scan mode. Also, the center of the measuring beam 106 is adjusted to coincide with the rotation center of the mirror of the XY scanner 119. The lenses 135-9 and 135-10 form an optical system for scanning the retina 127, and play a role in scanning the retina 127 with the measuring beam 106 using the vicinity of the cornea 126 as a pupil of the optical system. In this embodiment, the focus distances of the lenses 135-9 and 135-10 are 50 mm and 40 mm, respectively. Also, an electrical stage 117-2 can move in the directions shown by the arrow, and adjust and control a position of the attached lens 135-10. By adjusting the position of the lens 135-10, the measuring beam 106 can be focused on a predetermined layer in the retina 127 in the eye 107 to be inspected, and thereby observation can be performed. Also, the case of the eye 107 to be inspected having a refractive error can be addressed. When the measuring beam 106 is projected in the eye 107 to be inspected, it is reflected or scattered by the retina 127 to form the return beam 108, which is directed by the optical coupler 131 again to arrive at the line camera 139. The electrical stage 117-2 can be controlled by the personal computer 125, which characterizes the present exemplary embodiment.

Also, a part of the return beam 108 split by the beam splitter 158-2 is projected on the wavefront sensor 155, and an aberration of the return beam 108 is measured. The wavefront sensor 155 is electrically connected to the personal computer 125. The obtained aberration is expressed by using the personal computer 125 in a Zernike polynomial, which shows an aberration contained in the eye 107 to be inspected. The obtained aberration is expressed in the Zernike polynomial. Further, the position of the lens 135-10 is controlled by using the electrical stage 117-2 so that a defocus component in the Zernike polynomial can be corrected. A component except the defocus component can be corrected by controlling the form of the surface of the deformable mirror 159, which characterizes the exemplary embodiment. Here, the lenses 135-5, 135-6, 135-7, 135-8, 135-9 and 135-10 are disposed so that the cornea 126, the XY scanner 119, the wavefront sensor 155 and the deformable mirror 159 become optically conjugate with each other, and thereby the wavefront sensor 155 can measure an aberration contained in the eye 107 to be inspected. Here, the lens 135-10 used is a spherical lens, but a cylindrical lens may be used for the lens 135-10 dependent on an aberration (refractive error) in the eye 107 to be inspected. Also, another lens may be added to the light path of the measuring beam 106. A cylindrical lens can effectively correct the astigmatism in the Zernike polynomial, and also is effective in the case where an eye 107 to be inspected is astigmatic. Further, the position of the lens 135-10 is adjusted and controlled based on the obtained aberration, and the measuring beam 106 is kept focused on a predetermined layer in the retina 127, and then the form of the surface of the deformable mirror 159 is controlled. Thus, an aberration produced in the eye 107 to be inspected is corrected, and thereby a tomographic image can be provided with a higher lateral resolution.

Next, a configuration of a measuring system in the OCT apparatus of the exemplary embodiment is described. The OCT apparatus 100 can provide a tomographic image (OCT image) formed of intensities of an interference signal generated by a Mickelson interference system. This measuring system is described. The return beam 108 which is a beam reflected or scattered by the retina 127 is combined with the reference beam 105 by the optical coupler 131. Then, the combined beam 142 passes through the optical fiber 130-3 and the lens 135-2 and is projected on the transmission grating 141. Also, the combined beam 142 is dispersed into its wavelength components by the transmission grating 141, which are condensed by the lens 135-2, and light intensities are converted into a voltage for each of positions (wavelengths) by the line camera 139. Specifically, an interference pattern in a spectral region in the wavelength axis will be observed on the line camera 139.

The obtained group of voltage signals are converted into digital values by the frame grabber 140, which are data processed by the personal computer 125 to form a tomographic image. Here, the line camera 139 has 1024 pixels, and can provide intensities of the combined beam 142 for each of wavelengths (1024 division). Also, a part of the return beam 108 split by the beam splitter 158-2 is projected on the wavefront sensor 155, and an aberration of the return beam 108 is measured. The wavefront sensor 155 is of the Shack-Hartmann system. The obtained aberration is expressed in a Zernike polynomial, which expresses an aberration of the eye 107 to be inspected. The Zernike polynomial includes terms of tilt, defocus, astigmatism, coma, trefoil, etc. Note that the method for acquiring a tomographic image using an OCT apparatus is identical to that of the first exemplary embodiment, and a description thereof is omitted. The OCT apparatus 100 can provide a tomographic image of the retina 127 by controlling the XY scanner 119 and acquiring an interference pattern using the line camera 139.

Next, there is given a description of a procedure which characterizes the present embodiment for acquiring a tomographic image using an OCT apparatus with reference to FIGS. 5, 6A, 6B, 6C, 6D, 6E, and 7. Here, in the OCT apparatus 100, an aberration, generated in the eye to be inspected, of a measuring beam or a return beam is corrected by controlling the form of the surface of the deformable mirror 159 based on an aberration in the eye 107 to be inspected detected by the wavefront sensor 155, and thereby a tomographic image can be provided with a higher lateral resolution. Further, the aberration is kept corrected using the deformable mirror 159, and the position of the lens 135-10 is controlled using the electrical stage 117-2, and thus two tomographic images are acquired and composited with each other, and thereby a tomographic image can be provided with a high lateral resolution (see FIG. 5). In this embodiment the two tomographic images are acquired, but the number of tomographic images to be acquired may be any number. Particularly, if the beam diameter of the measuring beam is large, the depth of focus of the measuring beam 106 becomes short, and accordingly acquiring and compositing many tomographic images are effective.

FIGS. 6A, 6B, 6C, 6D and 6E illustrate procedures of the OCT apparatus 100 for acquiring a tomographic image. Here, a device for acquiring a tomographic image of the retina 127 in a myopic eye 107 to be inspected is described. The method for acquiring a tomographic image is such that the following steps (1) to (7) are, for example, successively executed in this order. Alternatively, the steps may return suitably. Also, the method may be configured so that the following steps are automatically executed using a computer, etc. FIG. 7 is a flow diagram for illustrating a procedure for acquiring a tomographic image described above.

(1) At step 1 (S21 in FIG. 7), while an eye 107 to be inspected is fixed to a fixation lamp 156, the measuring beam 106 is irradiated to the eye 107 to be inspected. In this embodiment, the position of the lens 135-10 is adjusted so that the measuring beam 106 is irradiated to the eye 107 to be inspected while being kept in a collimated beam (see FIG. 6A). The beam diameter of the measuring beam 106 is 2 mm, and the depth of focus is about 250 μm in the eye 107 to be inspected. Then, at step 2 (S22 in FIG. 7), the return beam 108 is measured by the wavefront sensor 155, and at step 3 (S23 in FIG. 7), an aberration of the return beam 108 is obtained (first step).

(2) The obtained aberration is converted into a Zernike polynomial by the personal computer 125, and a defocus component thereof is recorded in memory (second step). This expresses a diopter scale of the eye 107 to be inspected.

(3) At step 4 (S24 in FIG. 7), the position of the lens 135-10 is adjusted using the electrical stage 117-2 so that the defocus component is minimized (third step). Here, the measuring beam 106 is kept focused on the vicinity of the retinal pigment epithelium 127 (not shown) (see FIG. 6B).

(4) At step 5 (S25 in FIG. 7), the return beam 108 is measured by the wavefront sensor 155 to obtain an aberration of the eye 107 to be inspected. At step 6 (S26 in FIG. 7), the form of the surface of the deformable mirror 159 is controlled so that the obtained aberration is minimized (fourth step). In this embodiment, in order that the aberration is minimized, the form of the surface of the deformable mirror 159 is controlled in real time by means of feedback control using the wavefront sensor 155, the deformable mirror 159 and the personal computer 125. Here, the feedback control may be conducted without regard for one of the defocus component and an astigmatic component of the aberration, so that the high speed of the controlling is realized.

Figure 6A:
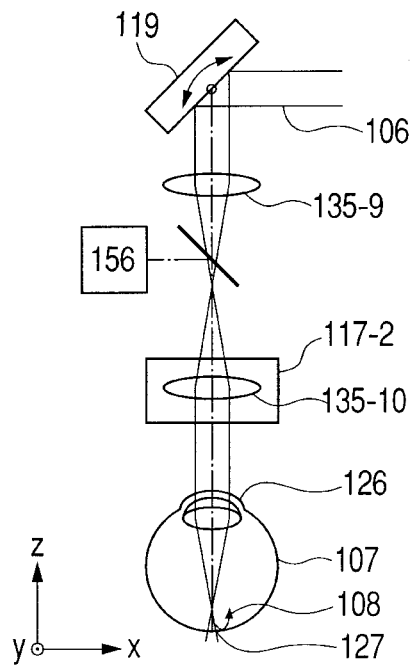
FIGS. 6A, 6B, 6C, 6D and 6E illustrate a method for acquiring a tomographic image of the OCT apparatus in the second exemplary embodiment of the present invention.
Figure 6B:
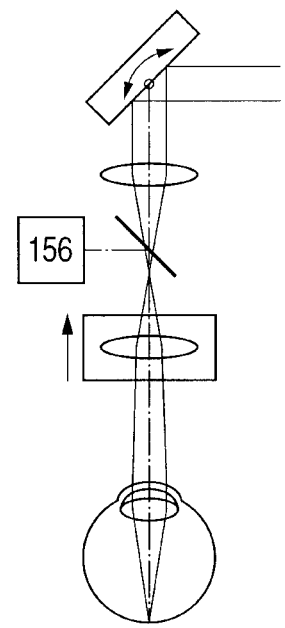
Figure 6C:
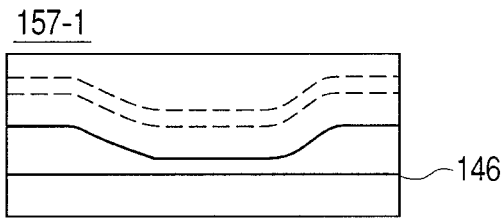
Figure 6D:
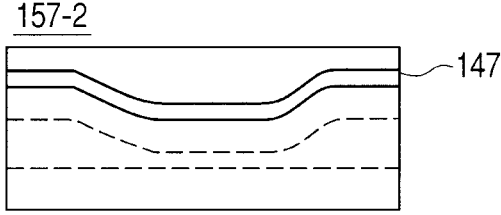

(5) At step 7 (S27 in FIG. 7), by detecting an interference pattern by the line sensor 139 while driving X axis of the XY scanner 119, a first tomographic image 157-1 (XZ plane) is obtained (see FIG. 6C). Here, dashed lines in the tomographic image 157 schematically illustrate that a lateral resolution and a contrast are low. That is, it is illustrated that the tomographic image 157-1 is imaged well at the vicinity of the retinal pigment epithelium 146.

(6) At step 8 (S28 in FIG. 7), the electrical stage 117-2 is controlled using the personal computer 125 to adjust the position of the lens 135-10 so that the measuring beam 106 is focused on the vicinity of the optic nerve fiber layer 147 (fifth step). Here, a displacement magnitude of the lens 135-10 is determined based on the diopter scale of the eye 107 to be inspected measured in the step (2). Then, at step 9 (S29 in FIG. 7), similar to the step (4) described above, a second tomographic image 157-2 is obtained (see FIG. 6D).

Figure 6E:
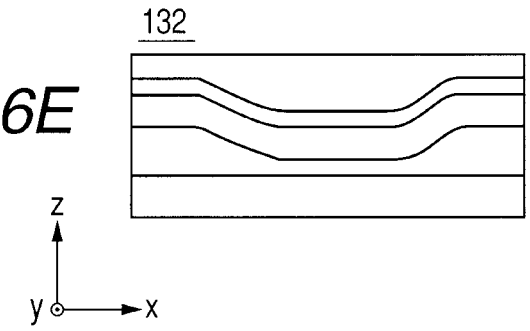

(7) At step 10 (S30 in FIG. 7), the first tomographic image 157-1 and the second tomographic image 157-2 are composited with each other to obtain a tomographic image 132 (see FIG. 6E). In this embodiment, the tomographic image 132 shows a good resolution and a good contrast in the whole measured region. Further, in the exemplary embodiment, because the aberration in the eye 107 to be inspected is corrected, a tomographic image can be provided with a high resolution and a high contrast, compared to the first exemplary embodiment.

Exemplary Embodiment 3

Figure 8:
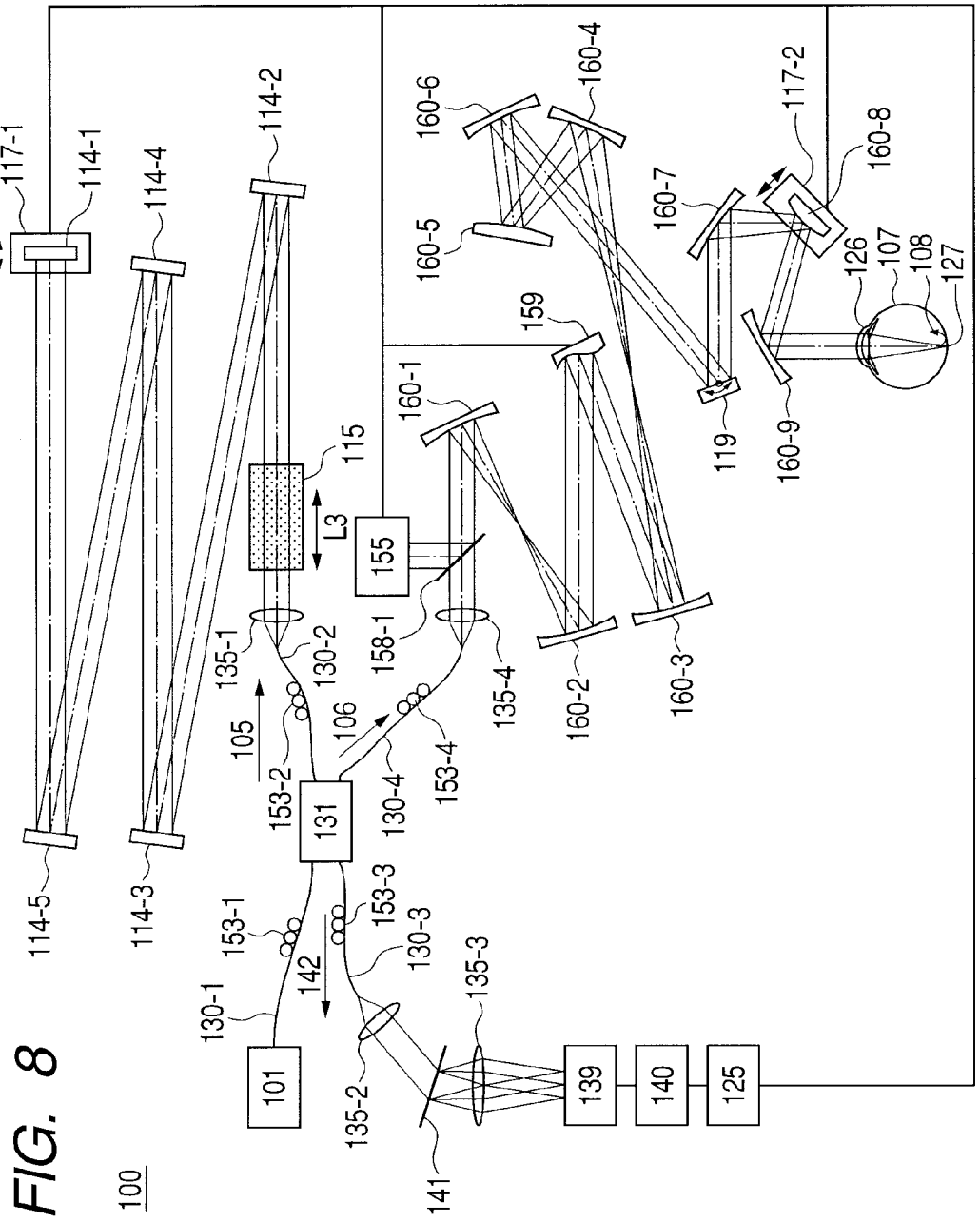
FIG. 8 illustrates a whole configuration of an OCT apparatus in a third exemplary embodiment of the present invention.

A third exemplary embodiment describes an OCT apparatus to which the present invention is applied. In this embodiment, particularly, there is given a description of an OCT apparatus with a high lateral resolution for imaging a tomographic image (OCT image) of an eye to be inspected. The present exemplary embodiment provides an OCT apparatus of the Fourier Domain system for acquiring a tomographic image by correcting an aberration in an eye to be inspected using a deformable mirror (as an aberration correcting device of the present embodiment), and the OCT apparatus is adapted so that a good tomographic image can be provided regardless of a diopter scale and/or an aberration in the eye to be inspected. In the exemplary embodiment, a whole optical system includes a reflective optical system mainly using spherical mirrors. Referring to FIG. 8, first, there is given a description of a whole, schematic configuration of an optical system of an OCT apparatus in the exemplary embodiment. In FIG. 8, a similar component to that of the second exemplary embodiment in FIG. 5 is designated by an identical symbol, and a description of a common part is omitted. In FIG. 8, mirrors are designated by the numbers 114-2, 114-3, 114-4, and 114-5, and spherical mirrors are designated by the numbers 160-1, 160-2, 160-3, 160-4, 160-5, 160-6, 160-7, 160-8 and 160-9.

An OCT apparatus 100 of the exemplary embodiment is, as illustrated in FIG. 8, a Michelson interference system as a whole. In FIG. 8, a beam emitted from a light source 101 passes through an optical fiber 130-1 and is split into a reference beam 105 and a measuring beam 106 with the ratio of 90:10 by an optical coupler 131. The measuring beam 106 is directed through an optical fiber 130-4, the spherical mirror 160-1, 160-2, 160-3, 160-4, 160-5, 160-6, 160-7, 160-8 and 160-9, a deformable mirror 159, an XY scanner 119, etc. to an eye 107 to be inspected as an object to be observed. Further, the measuring beam 106 is reflected or scattered at the eye 107 to be inspected to form a return beam 108, which comes back and is combined with the reference beam 105 by the optical coupler 131. The reference beam 105 and the return beam 108, after being combined, are projected on a line camera 139, and the obtained light intensities are used to form a tomographic image of the eye 107 to be inspected.

Next, details of the light source 101 are described. The light source 101 is a Super Luminescent Diode (SLD) which is a representative, low-coherence light source, and similar to the light source 101 of the first exemplary embodiment, and accordingly a description thereof is omitted. The beam emitted from the light source 101 passes through the single-mode fiber 130-1, and is directed to the optical coupler 131 and split into beams with the ratio of 90:10, which are the reference beam 105 and the measuring beam 106, respectively.

Next, a light path of the reference beam 105 is described. The reference beam 105 split by the optical coupler 131 passes through a single-mode fiber 130-2, and is directed to a lens 135-1 and adjusted to be a collimated beam having the beam diameter of 2 mm. Next, the reference beam 105 is directed through the mirrors 114-2, 114-3, 114-4 and 114-5 to a mirror 114-1 which is a reference mirror. Next, the reference beam 105 is reflected by the mirror 114-1 and directed back to the optical coupler 131. A dispersion compensation glass 115 through which the reference beam 105 passed compensates the reference beam 105 for dispersion produced when the measuring beam 106 goes to and comes back from the eye 107 to be inspected. The dispersion compensation glass 115 has the length of L3, and in this embodiment, it is set to L3=40 mm. Further, an electrical stage 117-1 can move in the directions shown by the arrow, and adjust and control the light path length of the reference beam 105. Also, the electrical stage 117-1 is controlled by a personal computer 125. Also, the light path length of the reference beam 105 is approximately equal to the light path length of the measuring beam 106 described below. Therefore, the light path length of the reference beam 105 is longer, compared to the second exemplary embodiment.

Next, a light path of the measuring beam 106 is described. The measuring beam 106 split by the optical coupler 131 passes through the single-mode fiber 130-4, and is directed to a lens 135-4 and adjusted to be a collimated beam having the beam diameter of 2 mm. The measuring beam 106 is projected through a beam splitter 158-1 and the spherical mirrors 160-1 and 160-2 on the deformable mirror 159. Here, the deformable mirror 159 is a mirror device for correcting an aberration of the measuring beam 106 and the return beam 108 by changing the mirror form thereof as desired, based on an aberration detected by a wavefront sensor 155. Here the deformable mirror has been used as a device for correcting an aberration, but the device may be any device capable of correcting an aberration, and a spatial light modulator using liquid crystal, etc. may be also used. Next, the measuring beam 106 passes through the lenses 160-3, 160-4, 160-5 and 160-6 and is projected on a mirror of the XY scanner 119. In this embodiment, for the simplicity, the XY scanner 119 is illustrated as one mirror, but actually the XY scanner 119 has two mirrors, a mirror for X scanning and a mirror for Y scanning, disposed close to each other therein, and scans the retina 127 in the direction perpendicular to the optical axis in the raster scan mode. Also, the center of the measuring beam 106 is adjusted to coincide with the rotation center of the mirror of the XY scanner 119. The spherical mirrors 160-7, 160-8 and 160-9 form an optical system for scanning the retina 127, and play a role in scanning the retina 127 with the measuring beam 106 using the vicinity of the cornea 126 as a pupil of the optical system. An electrical stage 117-2 can move in the directions shown by the arrow, and adjust and control a position of the attached spherical mirror 160-8. By adjusting the position of the spherical mirror 160-8, the measuring beam 106 can be focused on a predetermined layer in the retina 127 in the eye 107 to be inspected, and thereby observation of it can be performed. Also, the case of the eye 107 to be inspected having a refractive error can be addressed. When the measuring beam 106 is projected in the eye 107 to be inspected, it is reflected or scattered by the retina 127 to form the return beam 108, which is directed by the optical coupler 131 again to arrive at the line camera 139. The electrical stage 117-2 can be controlled by the personal computer 125, which characterizes the present embodiment.

Also, a part of the return beam 108 split by the beam splitter 158-1 is projected on the wavefront sensor 155, and an aberration of the return beam 108 is measured. The wavefront sensor 155 is electrically connected to the personal computer 125. The obtained aberration is expressed by using the personal computer 125 in a Zernike polynomial, which shows an aberration contained in the eye 107 to be inspected. The obtained aberration is expressed in the Zernike polynomial, which characterizes the present embodiment. Further, a defocus component in the Zernike polynomial can be corrected by controlling the position of the spherical mirror 160-8 using the electrical stage 117-2. A component except the defocus component can be corrected by controlling the form of the surface of the deformable mirror 159, which characterizes the present embodiment. In this embodiment, the spherical mirrors 160-1, 160-2, 160-3, 160-4, 160-5, 160-6, 160-7, 160-8 and 160-9 are disposed so that the cornea 126, the XY scanner 119, the wavefront sensor 155 and the deformable mirror 159 become optically conjugate with each other, and thereby the wavefront sensor 155 can measure an aberration contained in the eye 107 to be inspected. Further, the position of the spherical mirror 160-8 is adjusted and controlled based on the obtained aberration, and the measuring beam 106 is kept focused on a predetermined layer in the retina 127, and then the form of the surface of the deformable mirror 159 is controlled. Thus, an aberration produced in the eye 107 to be inspected is corrected, and thereby a tomographic image can be provided with a higher lateral resolution.

The reference beam 105 and the return beam 108 described above are combined with each other by the optical coupler 131, and further the combined beam 142 is split with the ratio of 90:10. Then, the combined beam 142 is dispersed into its wavelength components by a transmission grating 141, which are condensed by a lens 135-3, and light intensities are converted into a voltage for each of positions (wavelengths) by the line camera 139. Specifically, an interference pattern in a spectral region in the wavelength axis will be observed on the line camera 139. The obtained group of voltage signals are converted into digital values by a frame grabber 140, which are data processed by the personal computer 125 to form a tomographic image. In this embodiment, the line camera 139 has 1024 pixels, and the intensities of the combined beam 142 can be provided for each of wavelengths (1024 division).

Next, a configuration of a measuring system in the OCT apparatus of the exemplary embodiment is described. The OCT apparatus 100 can provide a tomographic image (OCT image) formed of intensities of an interference signal generated by a Mickelson interference system. This measuring system is similar to the second exemplary embodiment, and a description thereof is omitted.

Next, there is given a description of a method which characterizes the present embodiment for acquiring a tomographic image using an OCT apparatus. The method for measuring the tomographic image is similar to the second exemplary embodiment, and a description thereof is omitted. However, here, the spherical mirror 160-8 instead of the lens 135-10 in the second exemplary embodiment is used to adjust the focus position of the measuring beam 106.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2009-113818, filed May 8, 2009, and 2010-047052, filed on Mar. 3, 2010, which is hereby incorporated by reference herein in its entirety.

The invention claimed is:

1. An optical imaging apparatus for acquiring a tomographic image of an object based on a combined beam in which a return beam formed of a measuring beam irradiated to the object and a reference beam corresponding to the measuring beam are combined, the apparatus comprising:
an optical unit configured to focus the measuring beam on the object;
an aberration measuring unit configured to measure an aberration of the return beam;
an adjusting unit configured to adjust the optical unit to adjust focus positions of the optical unit at different depth positions based on the measured aberration; and
an acquiring unit configured to acquire a plurality of tomographic images corresponding to the focus positions at different depth positions, respectively.

2. The optical imaging apparatus according to claim 1, wherein the adjusting unit is adapted to adjust the optical unit based on at least any one of a defocus component and an astigmatic component in a Zernike polynomial that expresses the aberration.

3. The optical imaging apparatus according to claim 2, wherein the optical unit includes a first lens,
wherein the apparatus further comprises a second lens, and
wherein the adjusting unit is adapted to adjust the first lens based on the defocus component and to adjust the second lens based on the astigmatic component after the adjustment of the first lens.

4. The optical imaging apparatus according to claim 3, wherein the adjusting unit is configured to insert the second lens into a light path of the measuring beam, based on the astigmatic component.

5. The optical imaging apparatus according to claim 2, further comprising:
an aberration correcting unit configured to correct an aberration of at least any one of the measuring beam and the return beam, based on an aberration excluding at least any one of the defocus component and the astigmatic component, after the adjusting unit has adjusted the optical unit.

6. The optical imaging apparatus according to claim 2, further comprising:
a cylindrical lens,
wherein the adjusting unit is adapted to adjust the cylindrical lens based on the astigmatic component.

7. The optical imaging apparatus according to claim 1, wherein the adjusting unit is adapted to adjust a position of the optical unit in a direction of an optical axis, and
wherein the acquiring unit is adapted to acquire one of the plurality of tomographic images at the position.

8. The optical imaging apparatus according to claim 1, further comprising:
a unit configured to split a beam from a light source into a measuring beam and a reference beam,
a unit configured to combine a return beam formed of the measuring beam irradiated to the object and the reference beam traveling a reference light path to interfere with each other, and
a unit configured to detect intensities of an interference signal generated from the interference.

9. The optical imaging apparatus according to claim 1, further comprising:
a generating unit configured to generate a tomographic image based on the plurality of tomographic images having a different focus position in a depth direction from each other.

10. The optical imaging apparatus according to claim 1, wherein the object is an eye to be inspected, and
wherein the apparatus further comprises a fixation target to which the eye to be inspected is fixed.

11. A method of acquiring a tomographic image of an object based on a combined beam in which a return beam formed of a measuring beam irradiated to the object and a reference beam corresponding to the measuring beam are combined, the method comprising:
measuring an aberration of the return beam;
adjusting an optical unit, to adjust focus positions of the optical unit at different depth positions based on the measured aberration, wherein the optical unit focuses the measuring beam on the object; and acquiring a plurality of tomographic images corresponding to the focus positions at different depth positions, respectively.

12. The method according to claim 11, wherein the adjustment of the optical unit is based on at least any one of a defocus component and an astigmatic component in a Zernike polynomial that expresses the aberration.

13. The method according to claim 11, wherein the optical unit includes a first lens,
   wherein the adjustment of the first lens is based on the defocus component, and
   wherein the method further comprises adjusting a second lens based on the astigmatic component after the adjustment of the first lens.

14. The method according to claim 13, further comprising:
   after adjusting the optical unit, correcting the aberration of one of the measuring beam and the return beam, based on one of the defocus component and the astigmatic component.

15. The method according to claim 11, wherein a position of the optical unit is adjusted in a direction of an optical axis, and
   wherein one of the plurality of tomographic images is acquired at the position.

16. The method according to claim 11, further comprising generating a tomographic image based on the plurality of tomographic images having a different focus position in a depth direction from each other.

17. A non-transitory computer readable medium storing a program that causes a computer to execute the method of claim 11.

18. An optical imaging apparatus for acquiring a tomographic image of an object based on a combined beam in which a return beam formed of a measuring beam irradiated to the object and a reference beam corresponding to the measuring beam are combined, the apparatus comprising:
   a cylindrical lens for focusing the measuring beam on the object;
   an aberration measuring unit configured to measure an aberration of the return beam;
   an adjusting unit configured to adjust the cylindrical lens to adjust focus positions of an optical means at different depth positions based on the measured aberration; and
   acquiring means for acquiring a plurality of tomographic images corresponding to the focus positions at different depth positions, respectively.

19. The optical imaging apparatus according to claim 18, wherein the adjusting unit comprises:
   a first adjusting unit configured to adjust a spherical lens that is placed on a light path of the measuring beam, based on a defocus component of a Zernike polynomial; and
   a second adjusting unit configured to adjust the cylindrical lens based on an astigmatic component of the Zernike polynomial after the adjustment of the spherical lens.

20. The optical imaging apparatus according to claim 18, wherein the adjusting unit is configured to insert the cylindrical lens into a light path of the measuring beam, based on an astigmatic component of a Zernike polynomial.

* * * * *